United States Patent
Martin

(10) Patent No.: US 9,955,688 B2
(45) Date of Patent: May 1, 2018

(54) BIOCIDAL ALDEHYDE COMPOSITION

(71) Applicant: Howard Martin, Potomac, MD (US)

(72) Inventor: Howard Martin, Potomac, MD (US)

( * ) Notice: Subject to any disclaimer, the term of this patent is extended or adjusted under 35 U.S.C. 154(b) by 0 days. days.

(21) Appl. No.: 15/212,404

(22) Filed: Jul. 18, 2016

(65) Prior Publication Data

US 2017/0013834 A1    Jan. 19, 2017

Related U.S. Application Data

(60) Provisional application No. 62/193,173, filed on Jul. 16, 2015.

(51) Int. Cl.
*A01N 35/04* (2006.01)
*A01N 33/12* (2006.01)

(52) U.S. Cl.
CPC .................................... *A01N 35/04* (2013.01)

(58) Field of Classification Search
CPC ................................ A01N 35/04; A01N 33/12
See application file for complete search history.

(56) References Cited

U.S. PATENT DOCUMENTS

2017/0002260 A1 *    1/2017    Navar ..................... C09K 8/605

\* cited by examiner

*Primary Examiner* — Kendra D Carter
(74) *Attorney, Agent, or Firm* — Royal W. Craig; Baker Donelson, PC

(57) ABSTRACT

A novel combination of a biocide (Glutaraldehyde), a surfactant (BAK), in an alcohol/water solution, plus functional excipients. The Glutaraldehyde and BAK are combined in specific concentrations in an alcohol-solution form, with the other functional excipients specifically for the intended application. An embodiment for the oil and gas recovery industry is described in which the excipients Glutaraldehyde and cidal agent and BAK surfactant synergistically improve oil recovery. An embodiment for the in the healthcare industry (e.g., medical instrument sterilization) is described in the form of an immersion solution, spray, or pre-moistened cleaning wipette, with excipients including Trienthanol Amine, Glycol Ether, and Sulfonic Acid and water. In both cases the Glutaraldehyde in combination with the BAK works in synergy to kill bacteria and especially SRBs more effectively. The foregoing constituents are combined in preferred concentrations within acceptable ranges to provide a synergistic neoteric formulation that combines biocidal molecules in a biological chemical system that actively transports itself into the cells, through biofilm and cell wall/membranes, thereby overcoming penetration restraints to improve kill and kill time, without the need for activation or any time or temperature control. This is an effective example of synergistic complementarity.

2 Claims, No Drawings

BIOCIDAL ALDEHYDE COMPOSITION

CROSS-REFERENCE TO RELATED APPLICATION(S)

The present application derives priority from U.S. Provisional Application Ser. No. 62/193,173 filed 16 Jul. 2015.

BACKGROUND OF THE INVENTION

1. Field of the Invention

The present invention relates to chemical disinfection and, more particularly, to an improved biocidal aldehyde composition particularly suited for secondary oil and gas recovery and/or medical surface sterilization in the form of an immersion solution, spray or wipe.

2. Description of the Background

The purpose of disinfection is to reduce microbial contamination to an innocuous level. There is a widespread need for effective antimicrobials across diverse industries, including for oil and gas recovery (for treatment, penetration and removal of biofilm), and for disinfection of surfaces in the form of an immersion solution, spray, or pre-moistened cleaning wipette, etc. For oil and gas, microorganism growth leads to biofilm formation, which contributes to corrosion, contamination of oil and gas, and degradation of drilling muds and blockage. There are a few existing commercial biocides that purport to solve the need. For surface disinfection in the medical field, the goal is true "sterilization", which per FDA requirement requires inactivation of 100% of all the living pathogens, not merely inactivation of some. A biocide that demonstrates only 90% cidal effectiveness is essentially ineffective due to the substantial bacterial rebound effect the remaining 10% will cause.

Chemical disinfection in the areas of health care, water treatment, oil/gas biocides have need to move into new areas of low environmental impacts while still maintaining an effective tidal component at the lowest concentrations possible. Unfortunately advances in microbial disinfection have been negligible. Singular chemistries have been the prevailing approach along with additive concepts. However these approaches tend not to provide the required effectiveness without increasing toxicity and environmental issues. New directions, and new "synergistic" biocidal combinations are necessary to meet new problems and the new environmental regulations.

For years developmental chemistries did not make proper use of chemical kinetics or cellular micro components. Solutions are either bacteriostatic or bactericidal depending on concentration, and a single-faceted targeted attack is only partially effective. However, the present inventor recognizes that a multi-faceted attack on the cell wall, membrane and cellular components of bacteria can be significantly more effective than a targeted attack. What is needed is a synergistic compound with superior activity against bacteria while maintaining low toxic effects. With a synergistic formulation, the cidal effects are enhanced at low toxic concentrations and low environmental effect.

The key to achieving this difficult combination effect is to develop a "synergistic" compound of two existing biocides with accelerant expedients that will exhibit this singular characteristic.

The standard biocide used in health care and oil/gas water treatment is Glutaraldeyhde. However, Glutaraldehyde requires time and temperature control (residence time of 45-90 minutes for disinfection, and controlled temperature of from 20 C to 25-30 C). Glutaraldehyde requires activation and dating to make it useful. Thus, proper usage entails a three step procedure and meticulous record-keeping regarding date of activation. It is shown by Flow Cytometry that Glutaraldehyde alone (Davison et al, Antimicrob Agents & Chemther, 2010) has little or no penetration of biofilm where the important sessile organism reside. The Glut requires the penetrating ability of benzalkoniom chloride (BAK). This was determined using the MetaMorph image analysis program. Biofilms treated with Glut retained intracellular fluorescence because the Glut did not permeabilize the cell membrane. The Glut will kill rapidly the planktonic but not biofilm protected organisms.

What is needed is a simple and improved one-step formulation that uses Glutaraldehyde in combination with other constituents for more effective disinfection/sterilization in industrial/commercial uses such as oil and gas recovery and medical surface sterilization. However, biocide combinations may be too additive or not enough to be effective. The constituents alone seldom achieve the desired effect because the requisite amounts and/or concentrations are too high. Biocides exhibit a biocidal "window" of peak effect. As their concentrations increase beyond this "window" their effectiveness degrades, and they also exceed low toxicity requirements.

Synergism is the superior and correct method to develop new formulations rather than additive. This is easily described by the typical Langmuir pattern, (L-shaped) which is indicative of a situation where as sites of drug uptake become filled, additional drug will find it difficult to find a vacant site. This illustrates the fallacy of someone believing that increasing drug concentration or volume for more effect. This is the "dose/concentration reaction." The curve representing the dose/response is diphasic, where in one case nothing more happens or in the second case, over concentration, it reverses itself thru membrane coagulation. It has also been found that sublethal concentrations actually may stimulate growth or resistance. There is a "window of effect." Another drug pattern uptake is called the "high affinity H pattern" where the drug molecule has a strong affinity for the cell which is ideal. Most antibacterial drugs fall between L and H patterns, the present invention being closer to the H pattern.

The present invention provides a combination approach that uses two compounds with two different mechanisms of action to create a neoteric approach to the twin effects of cidal effectiveness and biofilm reduction. The present invention uses a surfactant BAK in combination with Glutaraldehyde and other constituents for more effective disinfection/sterilization. The combination is synergistic, rather than additive, which increases the permeability effect. This effect enables the "multiple-hit" effect on the bacterial cell so the cidal effects of the acidic Glutaraldehyde are improved, without activator/buffer, to a superior effect. This can be expressed mathematically thru the "probabilistic effect" in a given time "t" if inactivating a site within the cell containing "n" such sites necessary for viability is $P=\{1-\exp(-kt)\}^n$ where n=intercept hits to bring death to the cell. The present formulation falls between L and H but is closer to H indicating superior uptake and therefore enabling it to be more effective as the cidal tests support.

A posteriori assessments of the formulation cannot predict future results. In light of the extremely unpredictable nature of combination biocides, results are not additive because reactions are not clearly defined until test results are provided. Theory must be validated by experimentation: biology and chemistry cannot work in any other way. The present inventor has found that concentration ratios are important in compound formulations along with proper ratios of the components, and the present invention optimizes both. The present invention provides a proven innovative, formulation which exemplifies the goal of superior cidal effects while maintaining a low environmental impact thru its outstanding synergy. This is a true synergy. By using this unique approach bacteria require a longer time frame to attempt resistance and bacterial resistant transferase is considerably slow to develop resulting in decreased toxicity to environment and improved effectiveness through the synergistic approach.

SUMMARY OF THE INVENTION

It is, therefore, an object of the present innovation to provide a novel strategy for potentiating and improving the cidal effectiveness of Glutaraldehyde by a synergistic formulation that combines cidal molecules with a biological chemical system via BAK that actively transports itself into the cells, through the biofilm and cell wall/membranes, thereby overcoming penetration restraints.

It is another object to improve cidal effectiveness against a broader range of refractory microorganisms within ecological and environmentally acceptable parameters, essentially yielding a green biocide.

These and other objects are accomplished by a novel combination of Glutaraldehyde, and a particular surfactant, BAK, in an alcohol/water solution, with functional excipients. The surfactant is benzalkonium chloride ("BAK"), a cationic surface-acting agent belonging to the quaternary ammonium group. BAK absorbs onto a surface and alters the free energy of that surface. The alcohol is preferably isopropyl alcohol. The BAK produces an inherent weak bacteriocidal effect and lowers surface tension and thus aids in the spread of the Glut on the biofilm covered surface where it is readily absorbed by the negative surfaces of proteins and bacteria. It thus serves as a binding agent between the Glut and the application surface. The BAK in its critical micellar concentration has excellent wetting properties. It spreads the cidal component Glutaraldehyde on the cell surface and increases depth of penetration. Thus, the BAK is synergistic to the Glutaraldehyde, and vice versa, resulting in a more effective combined biological chemical system that actively transports itself into the cells, through the biofilm and cell wall/membranes, thereby overcoming penetration restraints to improve kill and kill time, without the need for activation or any time or temperature control. This is an important and key effect enabling ease of use.

The Glutaraldehyde and BAK are combined in specific concentrations in an alcohol-solution form, with other functional excipients specifically for the intended application.

The embodiment for the in the healthcare industry (e.g., medical instrument sterilization) is described in the form of a an immersion solution, spray, or pre-moistened cleaning wipette, with excipients including Trienthanol Amine, Glycol Ether, and Sulfonic Acid and water while the embodiment for the oil and gas industry is in solution form.

In both cases the Glutaraldehyde in combination with the BAK works in synergy to kill bacteria and especially SRBs more effectively.

Other objects, features, and advantages of the present invention will become more apparent from the following detailed description of the preferred embodiments and certain modifications thereof.

DETAILED DESCRIPTION OF THE PREFERRED EMBODIMENT

The present invention is a solution with a synergistic complementarity of constituents that combine to improve the cidal effectiveness of Glutaraldehyde with the surfactant benzalkonium chloride (BAK) in an isopropyl-alcohol solution and with an excipient biological chemical system with a functional excipient to provide improved application-specific results.

For example, the oil and gas recovery industry has a need for treatment, penetration and removal of biofilm. Biofilm harbors bacteria that attack surfaces such as steel, and that coalesces with oil in pipelines causing blockage. Biofilm occurs naturally by the bacteria, fungii, algae, protozoa developing it, as a protective mechanism. Surface microorganisms exist in planktonic suspension rather than in biofilm and are easier to kill. The biofilm exist in an exopolysaccharide matrix thereby having different characteristics than the planktonic types. This requires a biochemical approach rather than a purely chemical biocide as in the prior art. Currently, in oil and gas recovery techniques, companies employ a calibrated force to control the biofilm by overcoming the tensile strength of the matrix material without damaging the integrity of the surface. These techniques are not successful. Several groups have now reported that biofilm bacteria exhibit more resistance to biocides. As in medicine, industrial surfaces (such as surfaces of storage tanks, pipelines, water circulating systems, and machinery) become colonized by biofilms. It is known that the anionic polysaccharide matrix (glycocalyx) affords considerable protection to these cells against antimicrobial agents. Essentially a physical barrier is erected against the penetration of the biocide. Along with the barrier concept other biological mechanisms are also involved such as enzyme formation, reduction of metabolism through quiescence, and general stress response leading to a new general biofilm phenotype. Thus, the oil and gas industry has a severe biofouling problem with the development of biofilm along with sulfate reducing bacteria that creates significant damage. The basic strategy of biofilm control is predicated on the use of chemicals to kill bacteria in the biofilm, to induce the natural sloughing of dead biofilm thus cleaning the surface. This chemical approach suffers from the limitation that the most effective antimicrobial agents do not penetrate the biofilm. It is very difficult to deliver enough cidal agent to destroy the bacteria within the biofilm, the key sessile organisms. These insidious and coated bacteria must be destroyed in order for water pipelines to function and clean the oil. The biofilm contains amongst its variety of microorganisms, SRBs, algae, fungi, aerobic, anaerobic and facultative bacteria. Planktonic type bacteria exist in an aqueous phase and are relatively easier to kill. It is however, the extracellular polymeric material that protects the attached or contained sessile organism that is the difficult one to eradicate. It is with these protected organisms that the present formulation excels at multiple levels of attack rather than the previous singular level.

The present invention provides a one-step formulation for disinfection/sterilization for secondary oil and gas recovery by addition to fracturing (frac) water as an aqueous solution additive. The formulation comprises a combination of the cationic surface-acting agent benzalkonium chloride ("BAK") along with the core Glutaraldehyde of formula $C_5H_8O_2$ in an isopropyl alcohol solution form with a controlled pH, plus environmentally-friendly application-specific excipients. The foregoing combination created a synergistic and unexpected improvement in biocidal effectiveness resulting in faster kill time. The Glutaraldehyde along with the BAK worked in synergy to kill the SRBs more effectively.

In an embodiment for healthcare (described below), the excipients are Trienthanol Amine, Glycol Ether, and Sulfonic Acid. For secondary oil and gas recovery, the excipients may include any of a biodegradable proppant, a soluble friction reducing chemical additive, and a wetting agent, drag reducing agent, and flocculating agent.

In both cases the Glutaraldehyde in combination with the BAK in an alcohol solution format work in synergy to kill the SRBs more effectively.

In accordance with the present invention, a core Glutaraldehyde is combined with the above-described BAK in an isopropyl alcohol/water solution, with other functional excipients as desired in the following preferred concentrations within acceptable concentrate ranges:

| Constituent | % by weight (preferred) | Acceptable Range |
| --- | --- | --- |
| Glutaraldehyde | 36% | 25-50% |
| BAK | 8% | 8-15% |
| Isopropyl Alcohol | 40% | 10-40% |

The pH range throughout can be pH 3 to pH 9. In use, the foregoing biocidal formulation is diluted to within a range of from 50 ppm to 1000 ppm upon aqueous addition to fracturing water for secondary oil and gas recovery from a well.

The multi-level mechanism of action is as follows. The Glutaraldehyde produces an inherent bacteriocidal effect. BAK lowers surface tension and thus aids in the spread of the Glut on the biofilm covered surface and serves as a binding agent between the Glut and the application surface. The BAK spreads the Glutaraldehyde on the cell surface and increases depth of penetration. Thus, the BAK and Glutaraldehyde are mutually synergistic in attacking and achieving the desired kill effect. Because BAK is a quaternary ammonium salt one would suppose that it would react adversely with the Glutaraldehyde and cause aldehyde consumption. For this reason it became mandatory to check the Glutaraldehyde content and determine if there was a decrease at the CMC. Our studies did not show any reduction in Glutaraldehyde when combined correctly with BAK. This is likely correct due to the small BAK concentration necessary to reach the CMC. The BAK addition did not alter the action of the mixture in both eukaryotic or prokaryotic cells. As a matter of fact it acted synergistically to enhance cidal effects due to its surfactant action.

Specifically, the surfactant (BAK) works at reducing the surface tension and due its superior wetting properties and critical micellar concentration assists in spreading and depth of penetration of the combined solution and the ability of BAK to transport the cidal component, Glutaraldehyde. BAK's ability to repel biofilm formation as well as penetrate is based upon the physico/chemical and steric changes provoked by hydrophobic changes and electrostatic repulsion. This is due to the positively charged nitrogen that reacts with the acidic phospholipids in the cell membrane. This is the area of penetration bringing along the Glut (cidal component) increasing surface pressure which decreases the adhesive potential by affecting the osmoregularity of bacterial adhesins. Therefore the doubling effect of BAK to assist the transportation of Glut is recognized enabling a lower concentration of Glut to be as or more effective than higher concentrations making to a greener, safer formulation. The BAK molecules at the proper concentration are saturated or at the critical micelle concentration (CMC). When the BAK is above the CMC and the surface tension is constant the best wetting properties are achieved. The stated BAK concentration is important since low doses can actually stimulate metabolic reactions as well as cause resistance. Again the proper importance of "concentration ratios" develops the full synergistic effect. In an example the pendant drop method was used to determine surface tension activity of BAK. Ten drops were measured with a precision balance to calculate surface energy. Tate's equation was used for calculation. It was concluded that the surface tension was reduced by approximately 53%. This illustrates that the addition of the BAK to the formulation permits a better spreading of the solution.

Glutaraldehyde is not a strong penetrator or destroyer of biofilm and requires the help of the surfactant BAK component to penetrate the biofilm in order to achieve its cidal effect. BAK is a cationic detergent expressing a high affinity to cell membrane properties, even more so than dual chain quaternary ammonium compounds. Also BAK toxicity is much less than the dual chain quats and therefore more environmentally friendly. The antibacterial potential of BAK relies on the changes provoked on the ionic resistance of the cell membranes.

Test Results

In experiments, biofilm communities of *E. faecalis* were created following the techniques of Bergenholtz and Chavez, J. Endo. Coating (2010), using the present formulation. The combination biocide showed reduced biofilm formation due to the ability to reduce the level of the adhesion mechanism of the bacteria. This was confirmed by a staining LIVE/DEAD assay. Separating the two components the Glut had a 45% kill while the BAK less so while measuring bio-volume the BAK was much more effective with a volume reduction of over 70 fold. Clearly, Glutaraldehyde alone is not as effective as BAK, nor vice versa. Together in "proper ratio" the formula is outstanding at reducing biofilm as well as killing the necessary bacteria. This synergy was confirmed by the fractional inhibitory concentration index (FICI). The FICI for a synergistic mixture, using checkerboard, gave the combination of Glut/BAK a 0.35 FICI which is inhibitory. [Greene et al., App Env Micro Vol 72: 5254-5259 (2006)]. Mixtures according to this test are synergistic when the lowest FICI is below 0.8 therefore giving credence to the present concept. Synergy of Glut/BAK is known but has not been fully tested since the tested material has been Glut/Quats (dual chains) and not BAK. However, the usefulness of combining biocides (Glut) and surfactants (BAK) as suggested and developed here have not been previously demonstrated with proper concentration ratios but merely suggestive without testing. The present determination of 4:1 (Glut:BAK), FICI independently determined, corrects this missing component to make an effective formulation. Strong synergy has been shown between Glut/BAK (FICI 0.35). The biofilm reduction/penetration ability of BAK combined with the broad spectrum biocidal activities of Glut enable and achieve, at lower concentrations, due to synergy, the destruction of the SRBs in oil/gas as well the pertinent bacteria in health care.

The tests show that reducing biofilm adhesion thru BAK action and killing bacteria via Glutaraldehyde is an excellent synergistic complimentary approach to eliminating the bacterial/biofilm problem. Moreover, by using this unique approach bacteria require a longer time frame to attempt resistance and bacterial resistant transferase is considerably slow to develop resulting in decreased toxicity to environment and improved effectiveness through the synergistic approach. Thus, use of the present combination biocide to treat biofilm before it forms will help reduce the ability of bacteria to form biofilm, keeping it in planktonic form, which is easier to kill. The present formulation can also be utilized to coat instruments and pipelines to reduce biofilm.

In addition to the foregoing, *E. Coli*, *P. aeruginosa*, *salmonella typhii*, and *kiebsiella* were tested using selective media and biochemical means. Disk diffusion methods were used testing disinfectant resistance by measuring zones of inhibition after eighteen hours of incubation. MICs of disinfectants were determined by agar dilution. The MIC for Glut was individually determined to be 0.3% and for BAK was 0.13%. This shows clearly that the optimum range of the combination concentration for maximum effectiveness is form 4× to 6× Glut to BAK at the minimal level dependent on organism resistance which was varied. The preferred determined exposure is actually 4× of Glut to BAK as determined by log reduction effectiveness. This was supported by running an MIC (inhibitory) versus a MBC (bactericidal) test. Using the McFarland standard on *E. coli*, with the combination Glut/BAK, the result was that the bactericidal amount was 2× the inhibitory amount in ppm. This was done via serial dilutions on media Nutrient Broth.

It is necessary in both health care and oil/gas to ensure that the organisms are 100% killed in order to avoid rapid rebound phenomena. It is shown by Flow Cytometry that Glutaraldehyde alone has little or no penetration of biofilm where the important sessile organism resides. [Davison et al, Antimicrob Agents & Chemther (2010)] The Glut requires the penetrating ability of BAK. This was determined using the MetaMorph image analysis program. Biofilms treated with Glut retained intracellular fluorescence because the Glut did not permeabilize the cell membrane. The Glut will rapidly kill the planktonic but not biofilm protected organisms. BAK shows peripheral penetration followed by inward migration of the surfactant. This was not very rapid as sorption occurred due to biomass. This illustrates that the physical, chemical and the biological phenomena are importantly different from one agent to another agent and that it requires a "novel leap of creativity" to be able to combine the two agents, successfully, into one highly effective synergistic formula. These processes can occur together but they are fundamentally different.

To enable the effective killing of bacteria in both planktonic and sessile states the BAK acts as a transport mechanism for the Glutaraldehyde carrying it into the biofilm. The BAK will first act on cells near the fluid/biofilm interface along with Glut. It will then progressively penetrate and act on the embedded cells along with its Glut partner. The penetration is radially symmetric, indicating diffusion or the use of water channels via convection as the responsible factor within the biofilm, carrying the main cidal component. Glutaraldehyde is relatively toxic and has some negative environmental factors as a stand-alone biocide even at use concentrations. BAK is much less toxic depending on concentration as it is used in contact lens disinfection and as a preservative but at low concentrations. Together in the present synergistic formulation it is at its least toxic compared to effective amounts of either constituent alone. A modified use-dilution test is used to determine kill time. Ten (10) ml of Glut/BAK was placed in sterile test tubes, 0.1 ml of bacterial suspension *P. aeruginosa* log 5 was added along with 5% bovine calf serum as organic load. At time intervals of 5, 10, 30 min from original zero time, 1 ml of mixture was taken and placed in 9 ml of Tween 80 inactivator in nutrient broth. One ml from this was used for pour plate method and the numbers were counted. The results showed that the combination of Glut/BAK has a synergistic action that enables the elimination of *P. aeruginosa*. *P. aeruginosa* is a known surrogate also for SRBs found in oil/water treatment.

The functionality of BAK in the present formulation is to allow uptake of the Glutaraldehyde antimicrobial by enabling penetration and assisting in the cidal mechanism. BAK acts as a phase-transfer catalyst facilitating the conveyance of Glut to its active sites. This is a necessity as some bacteria have built up resistance to each of the components alone. Due to incorrect concentrations or more correctly, sub-inhibitory concentration doses of BAK (Effect of sub-inhibitory concentrations of BAK on the competitiveness of *P aeruginosa* grown in continuous culture: McCay et al, Microbiology, 2010) and Glutaraldehyde (Emergence of Glutaraldehyde-resistant *P. aerginosa*: Tschudin-Sutter et al., Infect Control Hosp Epidemol, 2011) resistance to each chemical has developed. [Effect of antimicrobial residues on early adhesion and biofilm formation by wild-type and BAK adapted *P aeruginosa*: Machado, Graca, Sousa, Lopes, Periera; Biofouling, 2011, Univ. Minho, Braga, Portugal] This is an example of incorrect ratios as well as incorrect concentrations being applied.

Another test, the EN 1276 Quantitative Suspension test following Accuratus Lab protocol, was accomplished with bioburden of 0.6% bovine albumin/erythrocytes against *P aeruginosa*. This test is considered a good method for studying disinfectant cidal ability. Neutralization was by Tween 80. CFU was adjusted to $10^8$ per ml. The requirement for bactericidal activity is a $log_{10}$ reduction of 5 or greater. The reduction combination of Glut/BAK at the end of 60 minutes was 5.28 indicating the combination was effectively bactericidal.

Example #1

Medical Surface Sterilization

In accordance with another embodiment of the invention, the same core Glutaraldehyde/BAK/isopropyl alcohol complex is formed with the functional excipients for medical surface sterilization in the form of an immersion solution, spray, or pre-moistened cleaning wipette. The excipients include Trienthanol Amine, Glycol Ether, and Sulfonic Acid, all in the following concentrations:

| Constituent | Concentrate |
| --- | --- |
| Glutaraldehyde | 25-40% |
| BAK | 6-15% |
| Isopropyl Alcohol | 10-40% |
| Triethanol amine | 0.25-2% |
| Glycol Ether | 2%-6% |
| Sulfonic Acid | 0.2-3% |

One skilled in the art will understand that the foregoing relative ratios of the components is of paramount importance to achieving the strong synergy demonstrated herein. The preferred formula amount of constituents specifically indicated above is best suited for clinical usage, and the amounts/concentrations may vary for other uses as described below.

In order to enhance and compliment the key combination of Glut and BAK, the use levels of the excipients tri-ethanol amine (0.5% of overall solution) a weak surfactant, glycol Ether (4.0% of solution), sulfonic acid/T-Det N9.5 chemical name of 4-Nonylphenyl-polyethylene glycol (0.2% of solution) and citric acid (0.04% of water) are added. The glycol ether functions as a solublizer to improve the miscibility of the key components. It also helps to stabilize the formula due to its extreme solubility. It adds to the wetting properties of the formula thereby increasing surfactant properties. The sulfonic acid also improves water solubility and acts as a homogenous catalyst helping in detergent action to facilitate surfactant action. IPA is used as a further solvent along with water. The glycol ether is a water soluble, biodegradable, non-toxic solvent used for its inherent cidal effect and to prevent the wipette from drying out. Glycol Ether in combination with the specific glutaraldehyde/BAK/IPA solution boosts cidal effectiveness. Similarly, methanosulfonic acid and triethanolamine are known surfactants, but are not generally known to have a cidal effect and would not be expected to have synergism in combination with the specific glutaraldehyde/BAK/IPA solution to boost cidal effectiveness. These excipients are in small amounts within the formulation to aid and abet the synergistic action of the Glut and BAK.

The above-described formulation illustrates the improved kill, and improved kill time, all at normal 20 degrees C. Overall, the newly developed biologically designed chemical combination enhances biocidal effectiveness. This is accomplished by improving and opening the diffusion channels through the cell wall, leading to disruption of the cytoplasmic membrane. This is partly accomplished by adsorption of the cidal agent via the surfactant to the bacterial cell surface and through the cytoplasmic membrane.

Example #2

Oil and Gas

In accordance with this embodiment of the invention, the core glutaraldehyde is combined with the above-described BAK in an isopropyl alcohol/water solution, with other functional excipients as desired in the following preferred concentrations within acceptable ranges:

| Constituent | Acceptable Range |
| --- | --- |
| Glutaraldehyde | 25-50% |
| BAK | 8-15% |
| Isopropyl Alcohol | 10-40% |
| methylcellulose, ethylcelluolose or hydroxymethylcellolose | 0.2-0.5% by weight |
| pluronic block copolymer | 0.01% to 3.00% by weight |
| poly(ethylene oxide) (Polyox ™) | 10 ppm to 100 ppm (.1-1%) |
| Triethanol Amine | 10 ppm to 100 ppm (.1-1%) |
| Glycol Ether | 10 ppm to 100 ppm (.1-1%) |
| Sulfonic Acid | 10 ppm to 100 ppm (.1-1%) |

The pH range throughout can be pH 3 to pH 9. In use, the foregoing biocidal formulation is diluted to within a range of from 50 ppm to 1000 ppm upon aqueous addition to fracturing water for secondary oil and gas recovery from a well.

In use, coating with the above-described formula showed reduced biofilm formation due to the ability to reduce the level of the adhesion mechanism of the bacteria. This was confirmed by the staining LIVE/DEAD assay. Separating the two components, the Glutaraldehyde had a 45% kill while the BAK less so while measuring bio-volume the BAK was much more effective with a volume reduction of over 70× fold. Glutaraldehyde alone is not as effective as BAK. Together in proper ratio the formula is outstanding at reducing biofilm as well as killing the necessary bacteria, and provides an excellent synergistic complimentary approach to eliminating the bacterial/biofilm problem. Therefore it shows that for treatment of biofilm before it forms this combination will help reduce the ability of bacteria to form biofilm keeping them in planktonic form which is easier to kill.

An additional effect is as an anticorrosive. The BAK obeys Langmuir's isotherm as stainless steel showed directional adsorption for corrosion inhibition. [Corrosion inhibition and adsorption thermodynamics of BAK for stainless in mud acid solution: Zhao, Wu, Jiao; Liaoning Normal Univ., CNKI (2012)] However this leads to the problem of preconditioning failure (Role of BAK surface preconditioning in increased resistance of biofilms to removal and disinfection authors [2004, Pereira, Simoes, Machado, Vieira; CEB, Univ. do Minho, Braga, Portugal] if BAK were to be used alone. This necessitates the use of the present combination formula of BAK/Glut in order to maintain effectiveness. This is another example where a multi-faceted synergistic approach improves upon the present condition.

The reason *P aeruginosa* was chosen as the test strain is that it is an accepted surrogate for SRB. This continuous exposure has allowed *pseudomonas* to develop phenotype resistance and makes for a stringent test.

The significance of bacterial adaptive resistance to BAK is obviated and overcome by the inclusion of Glut; as long as the ratio/concentrations are correct. [Postadaptational resistance to BAK and subsequent physicochemical modifications of *Listeria Monocytogenes*: To, Favrin, Romanova, Griffiths; Appl Environ Microbial, 2002, Univ. Guelph Canada).] These studies show the importance of the proper combining of Glut with the BAK and ratio of the Glut with the BAK (concentration/ratio) in order to reduce/eliminate bacterial resistance. A further test support of the two differing mechanism of BAK and Glutaraldehyde is the report by Jaramillo et al. which points out that the repelling effects of surfaces coated with BAK were not linked to any cell membrane damage in itself but on the interference with cell mechanisms of adhesion thereby requiring a cidal component (Glut) to effect kill. [Jaramillo, Arriola, Safavai & Chavez, "Decreased bacterial adherence and biofilm growth on surfaces coated with BAK", Univs. Conn, Loma Linda, Malmo, Guadalajara (Endo; 2012)] This illustrates the outstanding effectiveness of the dual component formula which exemplifies the highly effective unexpected synergy of the present formulation. This is an extraordinary example of novel synergistic complementarity.

Having now fully set forth the preferred embodiment, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. A biocidal formulation comprising a tidal complex consisting of glutaraldehyde within a range of from 33-40% by weight, benzalkonium chloride (BAK) within a range of from 5-11% by weight, wherein said glutaraldehyde and BAK being present in a relative concentration of from 4:1 to 6:1 of glutaraldehyde to BAK by weight, Triethanol Amine, Glycol Ether, and Sulfonic Acid, all mixed in an isopropyl alcohol (IPA) and water solution comprising IPA within a range of from 10% to 60% by weight.

2. The biocidal formulation of claim 1, provided in a form of an immersion solution, spray, or pre-moistened cleaning wipette.

* * * * *